US007780617B2

(12) United States Patent
Tornatore et al.

(10) Patent No.: US 7,780,617 B2
(45) Date of Patent: Aug. 24, 2010

(54) TRACTION DEVICE USING A WINCH

(76) Inventors: Renee A. Tornatore, 5304 River Creek Ct., Prospect, KY (US) 40059; Neil Munhofen, 4095 Banbury Pl., Swansca, IL (US) 62226

( * ) Notice: Subject to any disclaimer, the term of this patent is extended or adjusted under 35 U.S.C. 154(b) by 202 days.

(21) Appl. No.: 12/071,016

(22) Filed: Feb. 14, 2008

(65) Prior Publication Data

US 2009/0209895 A1 Aug. 20, 2009

(51) Int. Cl.
*A61F 5/00* (2006.01)

(52) U.S. Cl. ........................................................ 602/34

(58) Field of Classification Search ..................... 602/1, 602/32–38, 39, 40; 5/600, 306, 307; 254/226, 254/242, 283, 334; 212/123
See application file for complete search history.

(56) References Cited

U.S. PATENT DOCUMENTS

| | | | | | |
|---|---|---|---|---|---|
| 3,403,675 | A | * | 10/1968 | Carr | 602/32 |
| 5,575,765 | A | * | 11/1996 | Foster | 602/32 |
| 5,667,461 | A | * | 9/1997 | Hall | 482/69 |
| 2003/0018287 | A1 | | 1/2003 | Gilliam | |
| 2006/0030807 | A1 | | 2/2006 | Starr | |
| 2006/0206046 | A1 | | 9/2006 | Saunders et al. | |
| 2006/0287627 | A1 | | 12/2006 | Johnson | |

* cited by examiner

*Primary Examiner*—Patricia M Bianco
*Assistant Examiner*—Tarla R Patel
(74) *Attorney, Agent, or Firm*—Richard C. Litman

(57) ABSTRACT

The traction device using a winch employs an array of components including winches, pulleys and elastic bands mounted on an upright frame. The arrangement of the components allows the device to be utilized for traction without the use of cumbersome weights. The upright frame is configured to ensure stability. The components, including scales and cables, are mounted on the frame.

14 Claims, 3 Drawing Sheets

TRACTION DEVICE USING A WINCH

BACKGROUND OF THE INVENTION

1. Field of the Invention

The present invention generally relates to medical devices. More specifically, the present invention is drawn to a traction device using a winch, the traction device being used for decompression and/or traction of the spine and the cervical, lumbar and thoracic muscles.

2. Description of the Related Art

Whether caused by injury, obesity or inactivity, back and neck pain has become the most prevalent complaint in the health care area and the leading cause of work loss and disability. It has been estimated that up to ninety percent of adults will suffer some form of back or neck pain at some times during their lives. Such pain can range from an annoying ache to a situation of disablement. Medical experts have long recognized that most back pain is caused when the spinal discs are compressed to the point that the discs exert pressure on nerves passing between the vertebrae. It is also recognized that traction applied to the spine will, in many instances, function to de-compress the discs and thereby alleviate the pain. The medical community would certainly welcome a device that would efficiently perform the traction and decompression functions. Thus, a traction device using a winch solving the aforementioned problems is desired.

SUMMARY OF THE INVENTION

The traction device using a winch employs an array of winches, pulleys and elastic bands mounted on an upright frame. The arrangement of the aforementioned components allows the device to be utilized for traction without the use of cumbersome weights. The upright frame is configured to ensure stability. The components, including scales and cables, are mounted on the frame in a manner to provide for longevity and safety.

Accordingly, the invention presents a traction device that can be utilized, without an array of weights, to decompress spinal discs and tension muscles in the cervical, lumbar and thoracic areas of the human body. The device is efficient, safe and easy to use. The invention provides for improved elements thereof in an arrangement for the purposes described that are inexpensive, dependable and fully effective in accomplishing their intended purposes.

These and other features of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
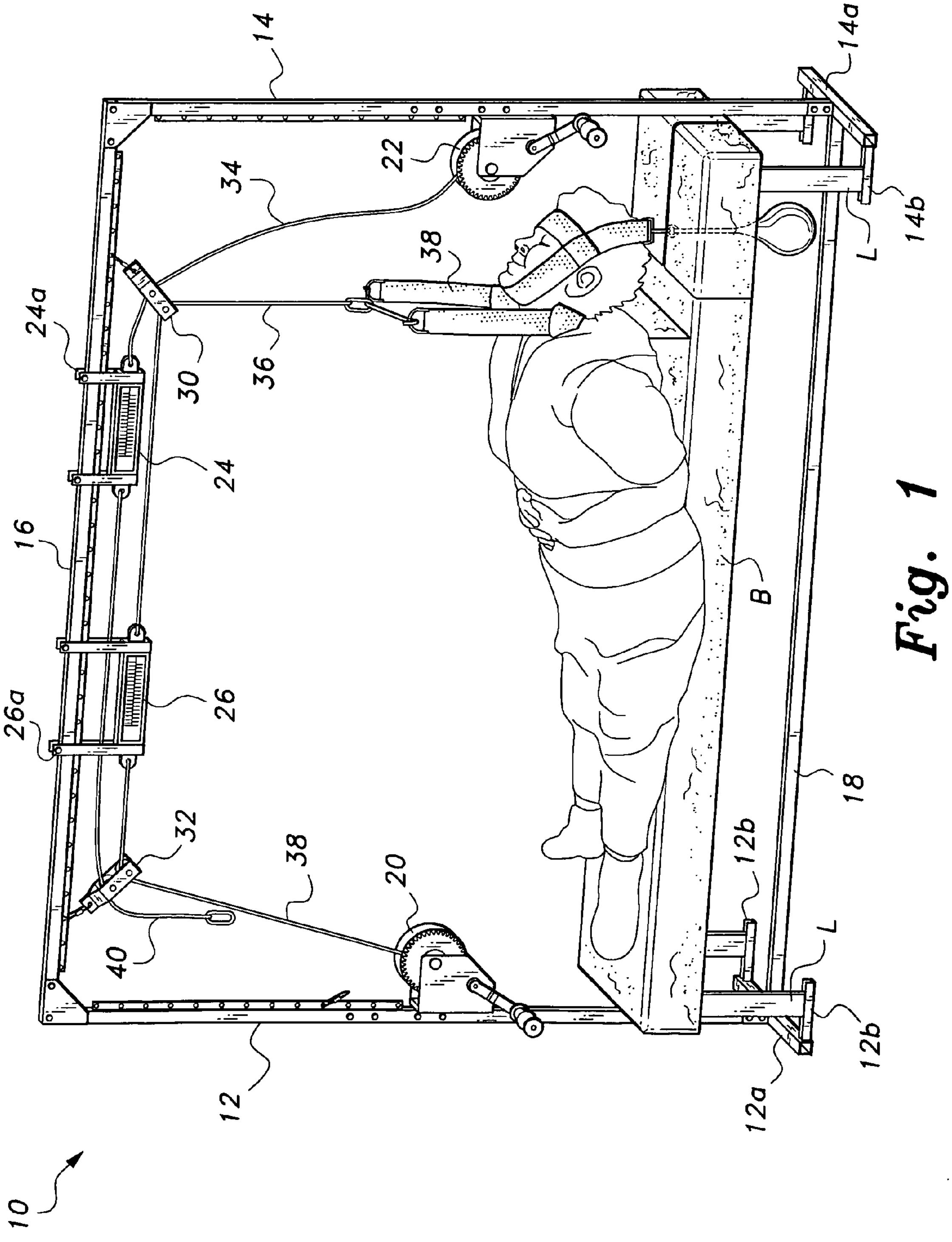
FIG. 1 is an environmental, perspective view of a traction device using a winch according to the present invention, shown configured for cervical traction.
Figure 2:
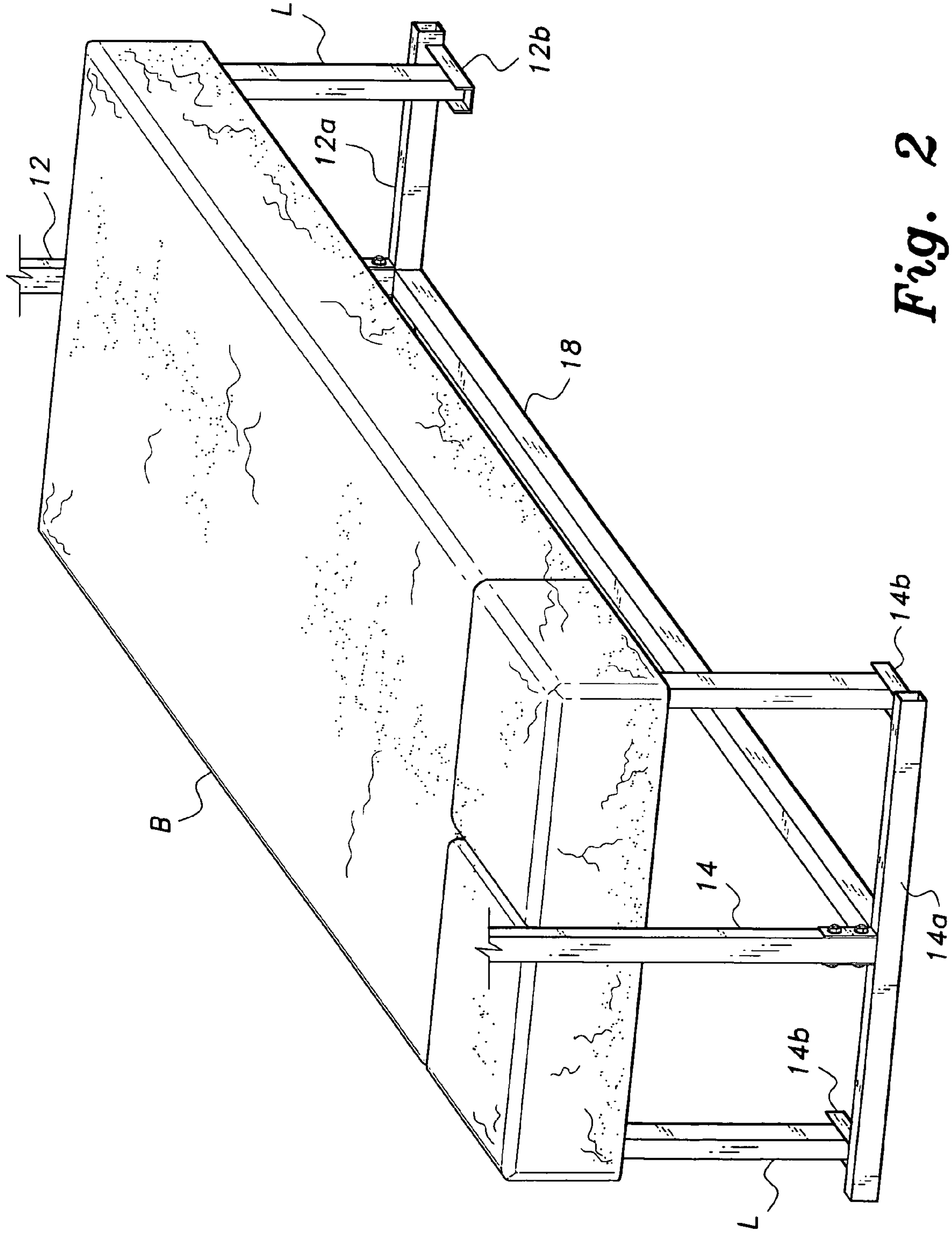
FIG. 2 is a partial, perspective end view of a traction device using a winch according to the present invention.

Attention is first directed to FIGS. 1 and 2, wherein the traction device is generally indicated at 10. Device 10 comprises a frame having vertical end members 12, 14 and a horizontally oriented overhead, member 16. The lower ends of vertical members 12 and 14 are respectively attached to a base comprising cross braces 12*a* and 14*a*, which braces are adapted to rest on a planar support surface such as a floor. A third brace 18 extends between braces 12*a* and 14*a* and is perpendicular thereto. Fasteners (including plates, bolts, nuts and the like) are employed to interconnect braces 12*a*, 14*a* and 18 with the lower ends of respective vertical members 12 and 14 and to attach overhead member 16 with the respective upper ends of vertical members 12 and 14. Each brace 12*a*, 14*a* is provided with respective pairs of channels 12*b*, 14*b* extending perpendicularly therefrom. Channels 12*b*, 14*b* are also adapted to rest on the planar support surface. Each respective pair of channels is spaced a pre-determined distance apart so as to receive the legs L of a traction bench B therein. This arrangement provides stability for the frame, preventing essentially any inadvertent frame movement during a traction procedure.

Each vertical member 12, 14 supports a respective winch 20, 22 thereon. Tension measuring scales 24 and 26 are supported on member 16 from respective brackets 24*a*, 26*a*. Respective pulleys 30, 32 are supported on member 16, each pulley positioned between a respective scale and a respective end of member 16. Each pulley is horizontally adjustable on member 16.

When used in a cervical traction mode (FIG. 1), an elastic cord 38 has a first end attached to winch 20 and a second end attached to scale 26 via pulley 32. Elastic cord 36 has a first end attached to cervical harness 38 and a second end attached to scale 26 via pulley 30. In use, the tension exerted by winch 20 is measured on scale 26, whereas the tension exerted on harness 38 is also measured on scale 26.

Figure 3:
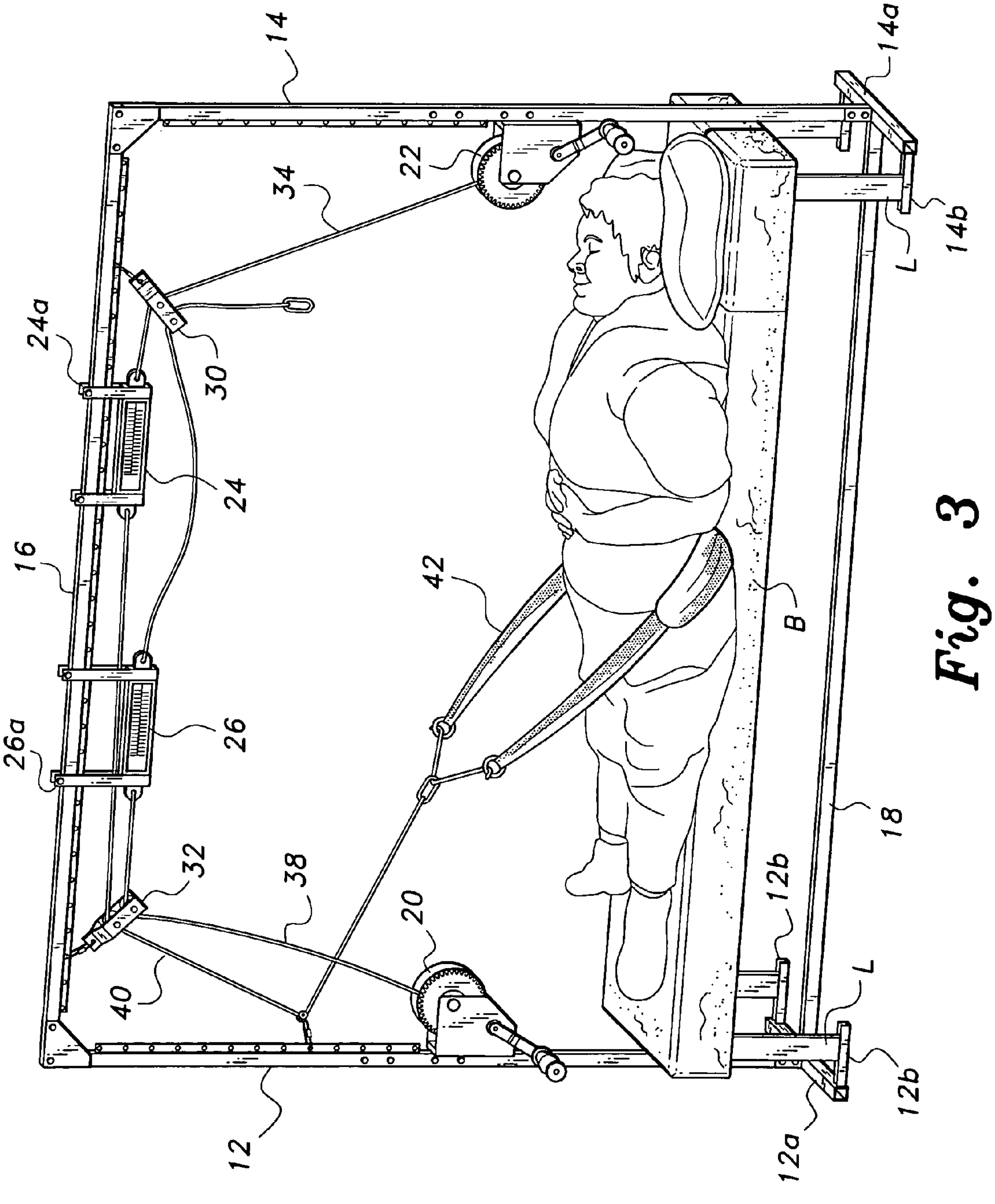
FIG. 3 is an environmental, perspective view of a traction device using a winch according to the present invention, shown configured for lumbar and thoracic traction.

In the lumbar and/or thoracic mode, as best seen in FIG. 3, an elastic cord 34 has one end attached to winch 22 and a second end attached to scale 24 via pulley 30. Elastic cord 40 has one end attached to lumbar or thoracic harness 42 and a second end attached to scale 24 via pulley 32. When the device is employed in the instant mode, the tension exerted by winch 22 is measured on scale 24, whereas the tension exerted on harness 42 is also measured on scale 24. It should be recognized that cervical and lumbar/thoracic traction can be accomplished together if necessary. This scenario would employ the use of both scales simultaneously. It is also contemplated that the scales may be coupled for a single traction procedure if desired.

It is to be understood that the present invention is not limited to the embodiment described above, but encompasses any and all embodiments within the scope of the following claims.

We claim:

1. A traction device, comprising:

a frame having a first end, a second end horizontally spaced a distance from the first end, a horizontal member connecting the first end to the second end, wherein the first end of the frame is a first vertical member having an upper end and a lower end and the second end of said frame is a second vertical member having an upper end and a lower end, the horizontal member spanning the distance between the first end and the second end, the horizontal member being attached to the upper end of the first vertical member and to the upper end of the second vertical member;

a first winch attached to the first vertical member;

a first tension measuring scale mounted directly on the horizontal member and substantially parallel thereto, the first tension measuring scale having a first end and a second end;

a first pulley mounted on the horizontal member adjacent the upper end of the first vertical member and between the first end of the tension measuring scale and a second pulley mounted on the horizontal member adjacent the upper end of the second vertical member and between the second end of the tension measuring scale;

a first cord having a first end attached to the first winch and a second end attached to the first end of the first tension measuring scale, the first cord being disposed about the first pulley;

a first traction harness; and a second cord having a first end attached to the second end of the first tension measuring scale and a second end attached to the traction harness, the second cord being disposed about the second pulley.

2. The traction device according to claim 1, wherein the first traction harness comprises a cervical traction harness.

3. The traction device according to claim 1, wherein the first traction harness comprises a lumbar and thoracic traction harness.

4. The traction device according to claim 1, further including a base attached to the lower ends of the first and second vertical members and a traction bench disposed on the base.

5. The traction device according to claim 1, further including a base attached to the lower ends of the first and second vertical members, the base having cross members, the cross members having channels thereon.

6. The traction device according to claim 5, further including a traction bench disposed on the base, wherein the bench has legs disposed in the channels.

7. The traction device according to claim 1, further including a second winch attached to the second vertical member, a second tension measuring scale mounted directly on the horizontal member and substantially parallel thereto, the second tension measuring scale having a first end and a second end, a third cord having a first end attached to the second winch and a second end attached to the first end of the second tension measuring scale, the third cord being disposed about the second pulley, a second traction harness, and a fourth cord having a first end attached to the second end of the second tension measuring scale and a second end attached to the second traction harness.

8. The traction device according to claim 7, wherein the second traction harness comprises a cervical traction harness.

9. The traction device according to claim 7, wherein the second traction harness comprises a lumbar and thoracic traction harness.

10. The traction device according to claim 7, wherein the third and fourth cords are elastic cords.

11. The traction device according to claim 7, wherein the second tension measuring scale is mounted on the horizontal member from a bracket.

12. The traction device according to claim 1, wherein the first and second cords are elastic cords.

13. The traction device according to claim 1, wherein the first tension measuring scale is mounted on the horizontal member from a bracket.

14. The traction device according to claim 1, wherein each of the pulleys is horizontally adjustable on the horizontal member.

* * * * *